(12) United States Patent
Fujii et al.

(10) Patent No.: US 11,877,765 B2
(45) Date of Patent: Jan. 23, 2024

(54) ENDOSCOPIC VESSEL HARVESTING DEVICES WITH CONDITIONING OF INSUFFLATION GAS

(71) Applicant: TERUMO CARDIOVASCULAR SYSTEMS CORPORATION, Ann Arbor, MI (US)

(72) Inventors: Tatsunori Fujii, Bear, DE (US); Randal J. Kadykowski, South Lyon, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 849 days.

(21) Appl. No.: 16/913,208

(22) Filed: Jun. 26, 2020

(65) Prior Publication Data

US 2021/0401451 A1    Dec. 30, 2021

(51) Int. Cl.
*A61B 17/32* (2006.01)
*A61B 17/3203* (2006.01)
(Continued)

(52) U.S. Cl.
CPC ...... *A61B 17/320016* (2013.01); *A61B 1/313* (2013.01); *A61B 17/00008* (2013.01); *A61B 17/3203* (2013.01); *A61B 17/3417* (2013.01); *A61B 17/3474* (2013.01); *A61B 90/36* (2016.02); *A61L 2/04* (2013.01); *A61L 2/10* (2013.01); *A61L 2/16* (2013.01); *A61M 1/784* (2021.05); *A61M 13/003* (2013.01); *A61B 2017/32035* (2013.01); *A61B 2017/320044* (2013.01); *A61B 2017/3419* (2013.01); *A61L 2/0005* (2013.01); *A61L 2202/22* (2013.01)

(58) Field of Classification Search
CPC ............ A61B 17/320016; A61B 1/313; A61B 17/00008; A61B 17/3417; A61B 17/3474; A61B 2017/320044; A61B 2017/32035; A61B 2017/3419; A61M 13/003
See application file for complete search history.

(56) References Cited

U.S. PATENT DOCUMENTS

| | | |
|---|---|---|
| 5,013,294 A | 5/1991 | Baier |
| 5,199,944 A | 4/1993 | Cosmescu |

(Continued)

FOREIGN PATENT DOCUMENTS

WO    WO-2007032017 A2 *    3/2007    ............. A61B 18/20

*Primary Examiner* — Adam Marcetich
(74) *Attorney, Agent, or Firm* — MacMillan, Sobanski & Todd, LLC

(57) ABSTRACT

A vessel harvesting apparatus for removing a blood vessel from a patient includes collection and conditioning (i.e., treatment) of expelled insufflation gas prior to releasing the gas into the air of the operating room. An endoscopic instrument has a distal end with a vessel harvesting tip and has a proximal end with a handle. An insufflation channel is configured to convey an insufflation gas subcutaneously into a dissected space within the patient. A removal channel is configured to evacuate fluidic contents from the dissected space, wherein the fluidic contents include insufflation gas and biological impurities. A processor/separator is coupled to the removal channel to process the fluidic contents to retain at least some of the biological impurities and to exhaust the insufflation gas.

18 Claims, 11 Drawing Sheets

(51) Int. Cl.
*A61B 17/34* (2006.01)
*A61B 90/00* (2016.01)
*A61M 13/00* (2006.01)
*A61B 1/313* (2006.01)
*A61M 1/00* (2006.01)
*A61L 2/16* (2006.01)
*A61L 2/10* (2006.01)
*A61L 2/04* (2006.01)
*A61B 17/00* (2006.01)
*A61L 2/00* (2006.01)

(56) References Cited

U.S. PATENT DOCUMENTS

| | | | |
|---|---|---|---|
| 5,688,256 A | 11/1997 | Surratt | |
| 5,779,662 A * | 7/1998 | Berman | A61B 17/32002 604/23 |
| 5,922,004 A * | 7/1999 | DuBois | A61B 1/00135 606/1 |
| 6,592,543 B1 * | 7/2003 | Wortrich | A61B 18/00 604/35 |
| 7,331,971 B2 | 2/2008 | Kasahara | |
| 7,335,159 B2 | 2/2008 | Banik | |
| 8,231,523 B2 | 7/2012 | Uesugi | |
| 8,337,412 B2 | 12/2012 | Fuller | |
| 8,414,576 B2 | 4/2013 | Cosmescu | |
| 8,608,715 B2 | 12/2013 | Roberts | |
| 8,920,456 B2 | 12/2014 | Kadykowski | |
| 9,987,439 B2 | 6/2018 | Williams | |
| 2004/0133228 A1 * | 7/2004 | Bayer | A61B 18/1482 606/190 |
| 2005/0015043 A1 * | 1/2005 | Stubbs | A61B 17/3423 604/164.01 |
| 2006/0036274 A1 * | 2/2006 | Usher | A61B 17/00008 606/190 |
| 2006/0052742 A1 * | 3/2006 | Ott | A61M 16/0051 604/23 |
| 2007/0005002 A1 * | 1/2007 | Millman | A61B 34/71 604/30 |
| 2013/0281780 A1 * | 10/2013 | Kadykowski | A61B 1/3132 600/116 |
| 2014/0188038 A1 * | 7/2014 | Stearns | A61B 17/3421 604/24 |
| 2014/0235954 A1 * | 8/2014 | Mohajer-Shojaee | A61B 17/3474 600/249 |
| 2015/0112246 A1 * | 4/2015 | Palmerton | A61M 13/003 96/400 |
| 2016/0183962 A1 * | 6/2016 | Spitz | A61B 17/3205 606/159 |
| 2017/0245910 A1 * | 8/2017 | Jinno | A61B 17/32 |
| 2018/0221598 A1 * | 8/2018 | Silver | A61B 1/015 |
| 2019/0008370 A1 * | 1/2019 | Hino | A61B 1/00119 |
| 2019/0159827 A1 * | 5/2019 | Horner | F24F 8/10 |
| 2019/0328983 A1 * | 10/2019 | Malkowski | A61M 13/003 |

* cited by examiner

ENDOSCOPIC VESSEL HARVESTING DEVICES WITH CONDITIONING OF INSUFFLATION GAS

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to devices and methods for endoscopic dissection of a blood vessel within the limb of a patient, and, more specifically, to devices using insufflation for opening a surgical tunnel around the blood vessel to be dissected/harvested.

In connection with coronary artery bypass grafting (CABG), a blood vessel or vessel section, such as an artery or vein, is "harvested" (i.e., removed) from its natural location in a patient's body to use it elsewhere in the body. In CABG surgery, the blood vessel is used to form a bypass between an arterial blood source and the coronary artery that is to be bypassed. Among the preferred sources for the vessel to be used as the bypass graft are the saphenous veins in the legs and the radial arteries in the arms.

Endoscopic surgical procedures for subcutaneously harvesting a section of a vein (e.g., the saphenous vein) have been developed in order to avoid disadvantages and potential complications of harvesting through a continuous incision. One such minimally-invasive technique employs a small incision for locating the desired vein and for introducing one or more endoscopic harvesting devices. Primary dissection occurs by introduction of a dissecting instrument through the incision to create a working space and separate the vein from the surrounding tissue. Then a cutting instrument is introduced into the working space to sever the blood vessel from the connective tissue and side branches of the blood vessel. The branches may be cauterized using the cutting instrument.

In one typical procedure, the endoscopic entry site is located near the midpoint of the vessel being harvested, with dissection and cutting of branches proceeding in both directions along the vessel from the entry site. In order to remove the desired section of the blood vessel, a second small incision, or stab wound, is made at one end thereof and the blood vessel section is ligated. A third small incision is made at the other end of the blood vessel section which is then ligated, thereby allowing the desired section to be completely removed through the first incision. Alternatively, only the first two incisions may be necessary if the length of the endoscopic device is sufficient to obtain the desired length of the blood vessel while working in only one direction along the vessel from the entry point.

An example of a commercially available product for performing the endoscopic vein harvesting described above is the VirtuoSaph Plus™ Endoscopic Vein Harvesting System from Terumo Cardiovascular Systems Corporation of Ann Arbor, Michigan. An endoscopic vein harvesting system of this type is also shown in U.S. Pat. Nos. 7,331,971 and 8,048,100 and U.S. patent application publications 2010/0292533 and 2012/0035606, which are incorporated herein by reference in their entirety.

The dissector tool typically comprises a longitudinal stainless steel or plastic rod with a tip at one end and an operator handle at the other. The tip is tapered to a blunt end and is made of transparent plastic. An endoscope including a camera or an optical cable is inserted through the hollow handle and hollow rod to abut the tip to allow for endoscopic viewing during dissection. The dissection proceeds along the perimeter of the vein being harvested to separate it from the surrounding tissue and to expose the side branches of the vein so that they can be severed with the cutting tool.

During dissection and cutting, an insufflation gas such as carbon dioxide ($CO_2$) is introduced to the subcutaneous space surrounding the blood vessel to improve visualization of the tissue structures within the operative tunnel being created around the vessel. The ability of the tunnel to be inflated may be facilitated in part by the use of a trocar at the entry site. Although closed (i.e., fully sealed) systems have been used wherein the insufflated gas remains trapped subcutaneously during the procedure, the trocar may preferably provide a partial seal around the endoscopic instrument. An open (i.e., partially sealed) system may avoid overpressurization of CO2 in the subcutaneous working space which could result in an embolism or intraluminal thrombus, for example. Since an open system does not provide a complete trocar seal by design, a continuous supply of the insufflation gas is provided through the endoscopic instrument which is delivered distally at its tip and leaks to the exterior from the incision site (e.g., trocar) or other leakage paths such as through non-sealed portions of the endoscopic instrument.

The insufflation gas is typically provided by a regulated source known as an insufflation device using a gas cylinder or a pipeline installed in a hospital setting. A target gas flow is set by the clinician, but the flow is normally modulated in order to ensure that a predetermined gas pressure is not exceeded within the surgical tunnel.

When insufflation gas is expelled from the working space, this leaked gas may possibly include particles that could pose a threat to health practitioners within the operating room. The insufflation gas acts as a fluid which mixes with other gasses, liquids, and suspended solids before being expelled. The particles may include biological impurities picked up by the insufflation gas such as a virus inhabiting the patient or smoke or gas vapor resulting from cauterization of connective tissue and side branches.

SUMMARY OF THE INVENTION

The present invention provides collection and conditioning (i.e., treatment) of expelled insufflation gas prior to releasing into the air of the operating room. In one aspect of the invention, a vessel harvesting apparatus is provided for removing a blood vessel from a patient. An endoscopic instrument has a distal end with a vessel harvesting tip and has a proximal end with a handle. An insufflation channel is configured to convey an insufflation gas subcutaneously into a dissected space within the patient. A removal channel is configured to evacuate fluidic contents from the dissected space, wherein the fluidic contents include insufflation gas and biological impurities. A separator is coupled to the removal channel to process the fluidic contents to retain at least some of the biological impurities and to exhaust the insufflation gas.

DETAILED DESCRIPTION OF PREFERRED EMBODIMENTS

Figure 1:
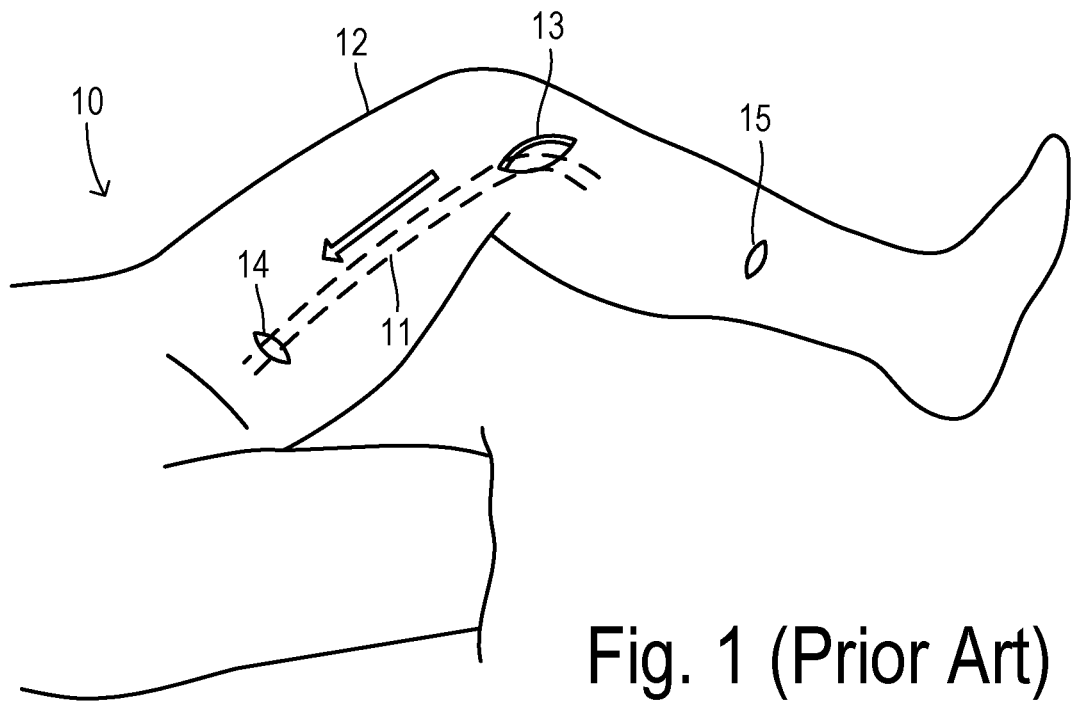
FIG. 1 is an external view of a saphenous vein being harvested from a leg.

Referring to FIG. 1, a patient 10 has a saphenous vein 11 within a lower limb 12. An incision 13 is made directly above vein 11, and tissue is peeled back from incision 13 to access the vein. Endoscopic instruments are inserted through incision 13 to separate vein 11 from connective tissue and then to sever and cauterize side branches that extend from vein 11. A second incision or stab wound 14 is created at a second position on limb 12 so that a second end of vein 11 can be severed. Vein 11 is then extracted through one of the incisions. The entry point and/or second incision or stab wound can be placed at various locations along vein 11 as shown at 15.

Figure 2:
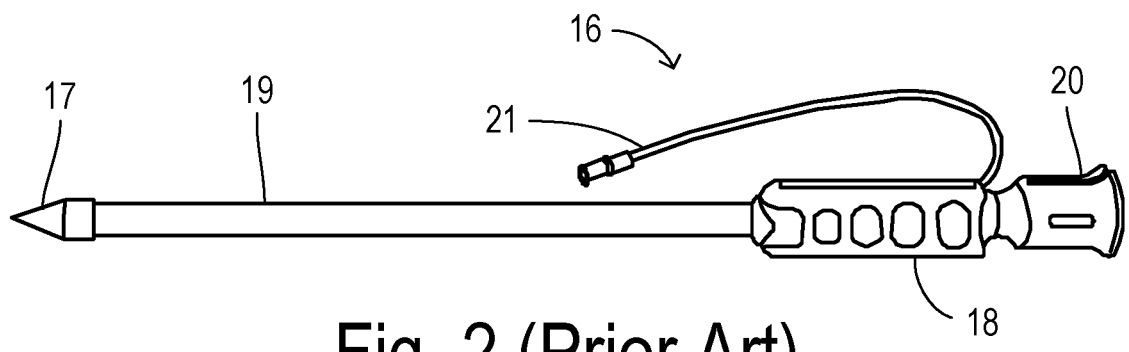
FIG. 2 is a side view of a prior art dissector unit.

A known dissector unit 16 is shown in FIG. 2 for endoscopic dissection of a saphenous vein or other vessel by insertion through an initial incision and then pressing a dissector tip 17 into the fat along the direction of the vessel to separate it from adjacent tissue. Dissector unit 16 has a handle 18 connected to a longitudinal rod 19 having dissector tip 17 at its distal end. A receiver 20 at the end of handle 18 receives an endoscope and optical cable (not shown) for extending through rod 19 to dissector tip 17 which is transparent in order to allow visualization of the vessel and surrounding tissue. An insufflation tube 21 passes through handle 12 and is part of an insufflation gas channel extending to a release hole in or near tip 17. Tube 21 is connected to a source of $CO_2$ or other insufflation gas for filling the cavity adjacent the vessel as it is being formed.

Figure 3:
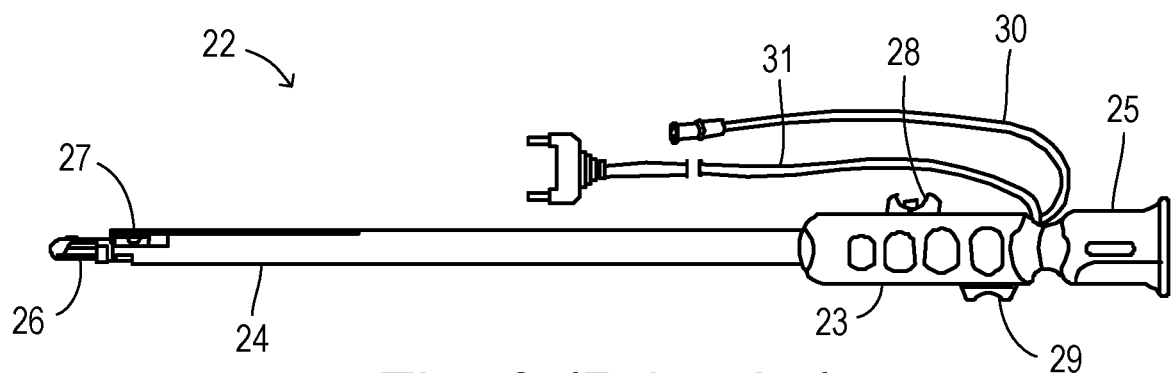
FIG. 3 is a side view of a prior art cutting unit.

After initial blunt dissection around the vessel, a harvester cutting unit 22 as shown in FIG. 3 is used subcutaneously to grasp the vessel being dissected and to sever any branches or connective tissue connecting to the vessel. Harvester 22 has a handle 23 connected to an elongated sleeve member 24 and an endoscope receiver 25. At the distal end of sleeve 24 are a vessel keeper (V-keeper) 26 for retaining the vessel being dissected and a vessel cutter (V-cutter) 27 for severing branches. V-keeper 26 is manipulated by V-keeper buttons 28 on handle 23. V-cutter 27 is extended or retracted by manipulating a V-cutter extender button 29 on handle 23. An insufflator tube 30 is adapted to be connected to an insufflation source to deliver the gas to the distal end of sleeve 24 via a gas channel extending between handle 23 at the proximal end and a release hole at the distal end. A bipolar or integrated bipolar cord 31 connects to a source of high frequency voltage, and includes conductors for supplying the voltage to electrodes on V-cutter 27 for cutting and cauterizing the branches and connective tissue.

Figure 4:
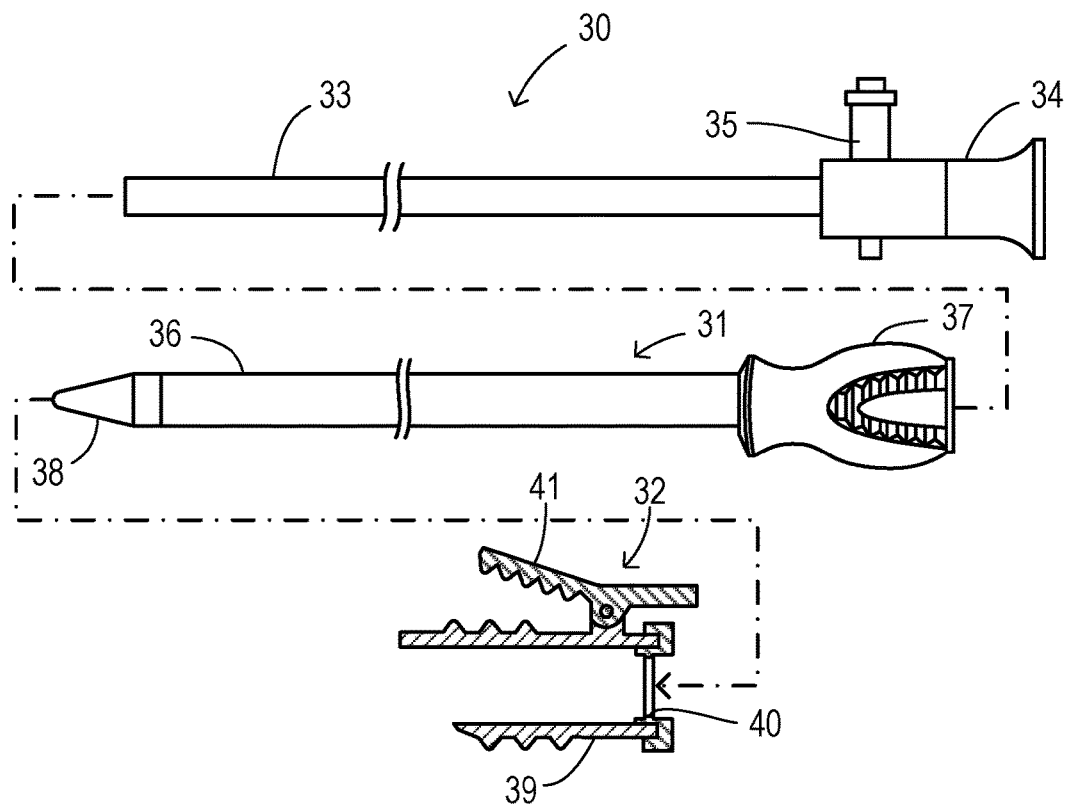
FIG. 4 is a plan view of a prior art blunt dissector with an endoscope and a trocar.

FIG. 4 shows another vessel harvesting system which includes an endoscope unit 30 to perform observation in a patient's body, a dissector unit 31 to dissect a blood vessel in the body, and a trocar 32 to help insert the endoscope 30 and dissector apparatus 31 into the body. An optical system is shown as a rigid endoscope 30 and includes an elongated rod-like inserting portion 33. The proximal end of inserting portion 33 connects to an end adapter 34 to transmit an endoscopic image. A light guide port 35 projects from end adapter 34 to connect to a light guide cable which supplies illumination light to endoscope 30. In other embodiments, the optical system can employ a camera and LED light source installed at the distal end of endoscope 30 connected via electrical cables to power and a video processor.

Dissector unit 31 includes a tubular main body portion 36 comprising a hollow longitudinal rod within which endoscope 30 is to be inserted. Endoscope 30 is inserted or removed from longitudinal rod 36 through a handle portion 37. The material of longitudinal rod 36 material is selected from fluoropolymers, which are well known materials. The most preferred material for constituting the outer surface of longitudinal rod 36 is polytetrafluoroethylene (PTFE). The use of a fluoropolymer reduces the friction caused by moving rod 36 through connective tissue, thereby reducing the force required to perform a dissection.

A blunt dissector tip 38 is disposed at the distal end of longitudinal rod 36. Tip 38 has a conical shape and comprises a transparent synthetic resin material to facilitate viewing through tip 38 using endoscope 30. Trocar 32 includes a body 39 to guide dissector unit 31 into the incision site. An aperture seal 40 is located on the surface of the proximal end of body 39. Aperture seal 40 allows dissector unit 31 to be inserted in body 39 of trocar 32 in one fluid forward motion. The outer surface of trocar body 39 includes a projection to engage with living tissue and a holding portion 41 to hold the body 39 onto the living tissue (e.g., patient's skin).

Figure 5:
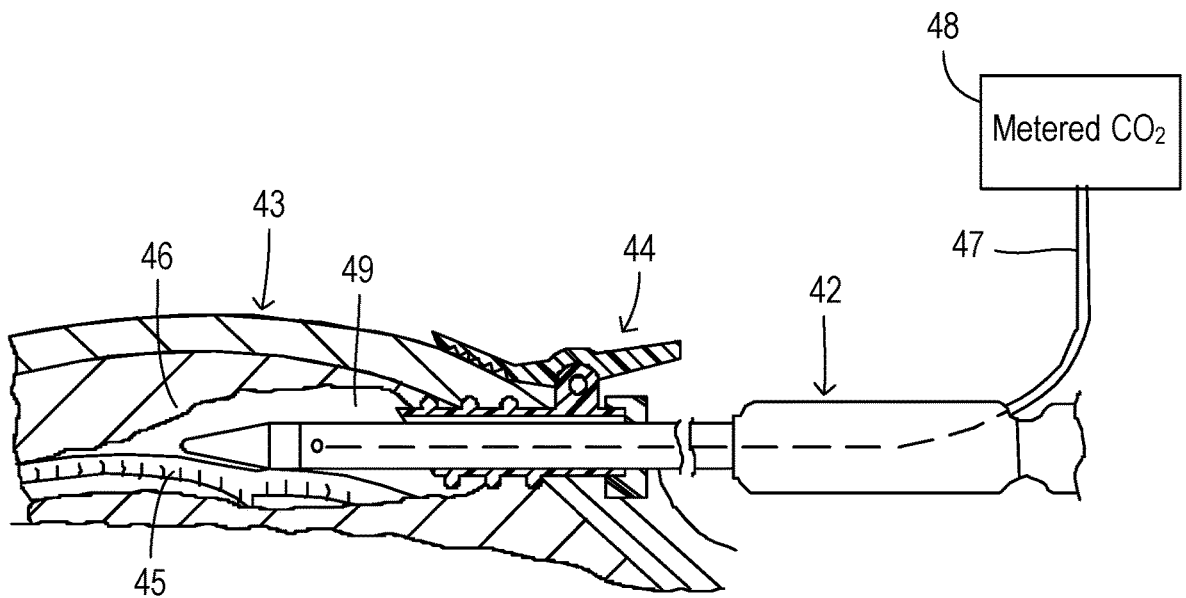
FIG. 5 is a partial cross-sectional view of the dissection of a blood vessel.

FIG. 5 is cross-sectional view showing a dissector unit 42 inserted subcutaneously within a lower limb 43 via a trocar 44 from a skin incision in the direction of the inguinal region, for example. Since the inserting direction of dissector 10 is along the direction of a blood vessel 45 being dissected, the operator gradually inserts the dissector so as to dissect peripheral tissue 46 from blood vessel 45 while viewing the endoscope image.

Figure 6:
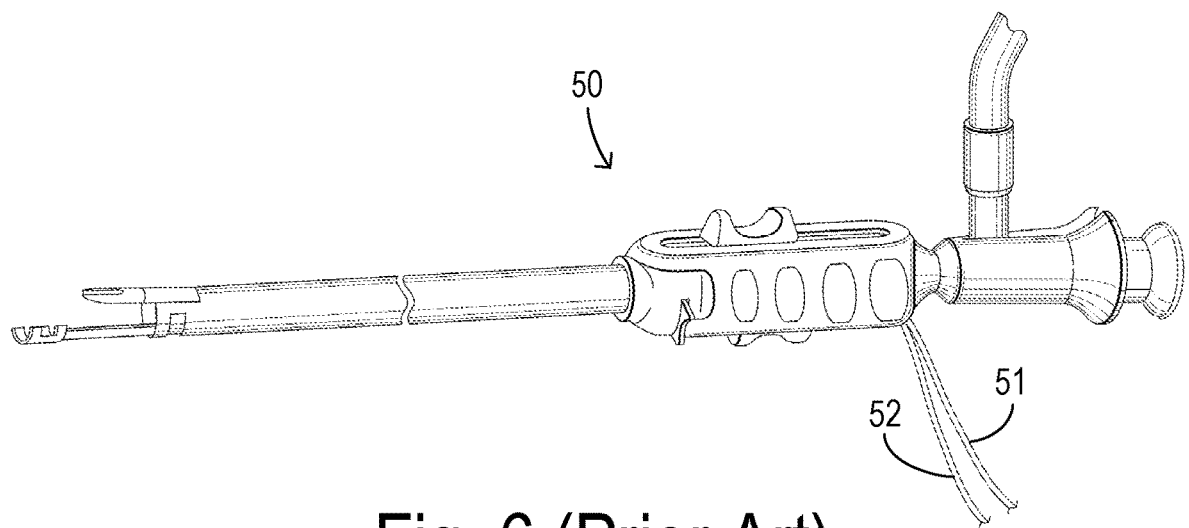
FIG. 6 schematically shows a prior art cutting unit in greater detail.

An insufflation gas (e.g., carbon dioxide) may be fed via a tube 47 from a regulated insufflation gas source 48. An insufflation unit such as the UHI-3 High Flow Insufflation Unit, available from Olympus Medical Systems Corporation, can be used. As blood vessel 35 is dissected from the peripheral tissue, the $CO_2$ gas inflates the area between the dissected tissue and the blood vessel to create an open tunnel 49. Therefore, the field of view of the endoscope is opened wide by gas inflation so that visualization of the internal tissue structures is improved. Following blunt dissection, a cutter unit is inserted through trocar 44 and tunnel 49 is insufflated in the same manner. A cutter unit 50 as shown in FIG. 6 can be used. An insufflation tube 51 can be connected to the same gas source. Cutter unit 50 is also connected to an electrical bipolar source via electrical cable 52.

Figure 7:
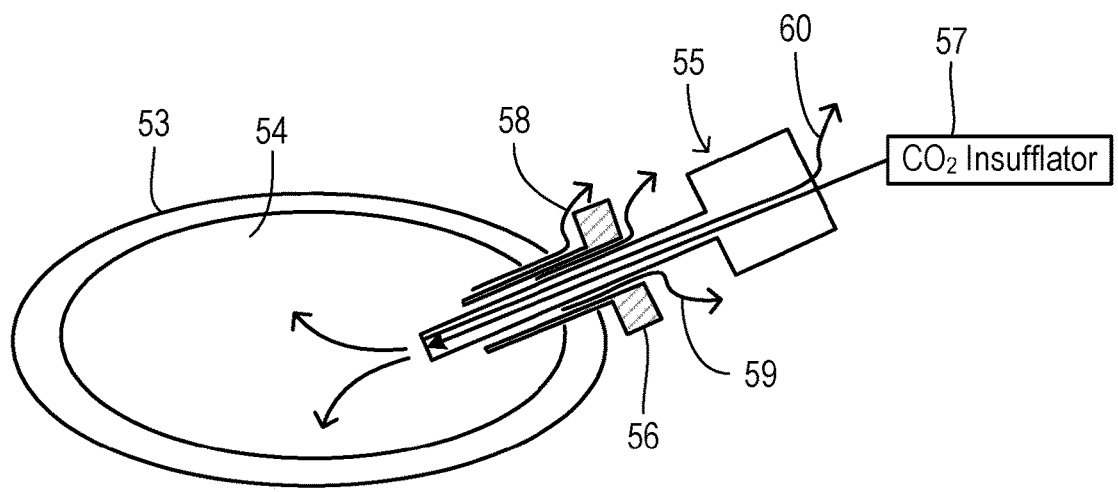
FIG. 7 is a diagram depicting leakage locations in a prior art harvesting unit using a trocar.

Typically, a regulated supply of insufflation gas has been delivered through an insufflation channel in the endoscopic instrument. The inflation gas is expelled out of the tip to inflate a tunnel within the patient. From the tunnel, various leakage paths have been present as shown in FIG. 7. An incision in a patient's body 53 provides access to a dissected tunnel 54, into which a trocar 56 and an endoscopic instrument 55 (e.g., a dissector unit or a cutter unit) are inserted. An insufflation source 56 provides insufflation gas through instrument 55 into tunnel 54. Leakage paths by which the insufflation gas exhausts into the ambient air of an operating room include a path 58 including a gap between patient's body 53 and trocar 56, a path 59 including a gap between trocar 56 and instrument 55, and a path 60 within instrument 55. Path 60 may or may not exist depending on the design of instrument 55. The surgical technique creating the interface between trocar 56 and body 53, the dimensions and materials of the interface between trocar 56 and instrument 55, and the internal properties of instrument 55 are adapted to provide a limited flow capacity of (i.e., a predetermined flow resistance in) paths 58, 59, and 60 so that a desired amount of gas pressure can be maintained in tunnel 54. Nevertheless, flow taking place through leakage paths 58-60 avoids overpressurization in tunnel 54.

Figure 8:
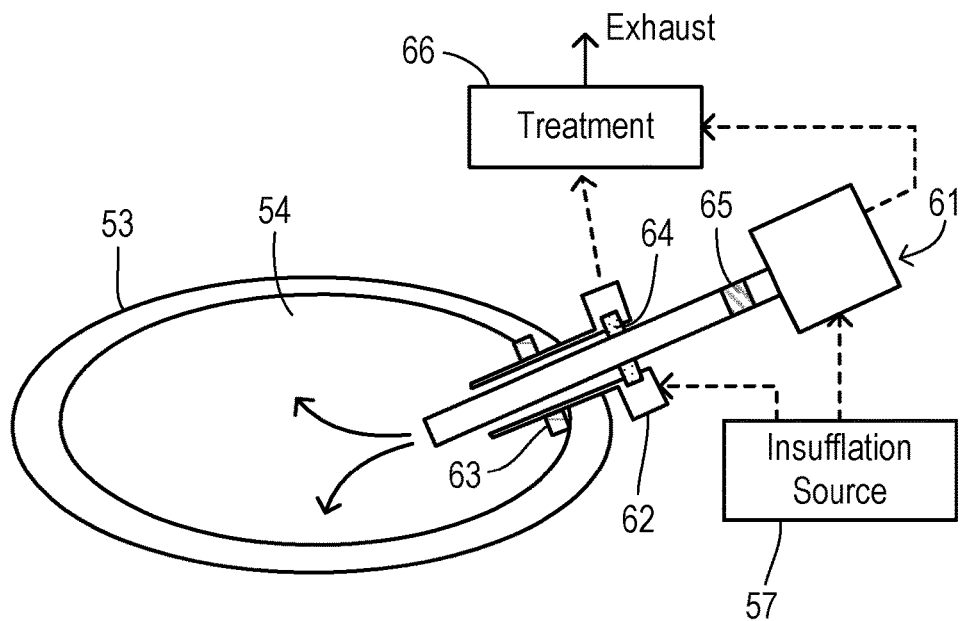
FIG. 8 is a diagram showing a sealed harvesting unit of the present invention for collecting and treating insufflation gas.

To avoid potential exposure to harmful biological impurities (e.g., suspended particles, liquids, and gaseous byproducts) within an uncontrolled release of leaked insufflation gas, the invention collects and treats insufflation gas prior to exhausting it into the ambient air as shown in FIG. 8. An endoscopic instrument 61 is inserted through a trocar 62 which is placed in an incision in body 53 and tunnel 54. To prevent uncontrolled leakage of insufflation gas, a sealing interface 63 is provided between body 53 and trocar 62, a sealing interface 64 is provided between trocar 62 and instrument 61, and a sealing interface 65 is maintained within instrument 61. The sealing interfaces may inherently result from the contact between and properties of the separate elements or may be provided by added sealing components (e.g., O-rings, gaskets, balloons, sponges, soft materials, and rubber). For example, the size and shape of an incision for inserting a trocar can be configured to achieve an adequate seal. When a trocar is not used, the size and shape of the incision can be configured to achieve an adequate seal directly to an endoscopic instrument that is being inserted without a trocar. To maintain the advantages of an open system, an insufflation gas removal channel is provided in instrument 61 and/or trocar 62 to collect fluidic contents (e.g., insufflation gas plus biological impurities) from tunnel 54 and convey them to a separator/treatment unit 66. In different embodiments of the invention, an insufflation channel for conveying the insufflation gas subcutaneously into the dissected tunnel can be disposed through endoscopic instrument 61 (e.g., extending from the proximal handle end to the distal tip end) or can be disposed in the trocar (e.g., integrated in a body of the trocar). Likewise, the removal channel for evacuating fluidic contents from the dissected tunnel can be disposed through endoscopic instrument 61 (e.g., extending from the proximal handle end to the distal tip end) or can be disposed in the trocar (e.g., integrated in a body of the trocar). After treatment in separator 66, an outflow of insufflation gas can be exhausted to the ambient air.

Processing of the removed fluidic contents within separator 66 can include one or more processes to address respective impurities that it may be desirable to mitigate. For example, solid particles (e.g., viruses or smoke particles from cauterization) may be filtered in separator 66 by passing the fluidic contents through a filter (e.g., HEPA filter) to confine particles having a predetermined minimum size (e.g., about 100 nm for Corona virus, about 80 nm for SARS virus, about 200 nm for *Rubella* virus, or in a range of about 80 nm to 120 nm for influenza virus, a range of about 100 nm to 600 nm for mumps, or a range of about 700 nm to 1200 nm for MRSA). Liquid impurities may be separated using a canister (e.g., containing adsorbent material) to provide a liquid trap. The separation processing can be comprised of sterilization of the fluidic contents prior to release. The sterilization can include application of heat, ultraviolet light, and/or a disinfectant substance (e.g., ethylene oxide or ozone).

Figure 9:
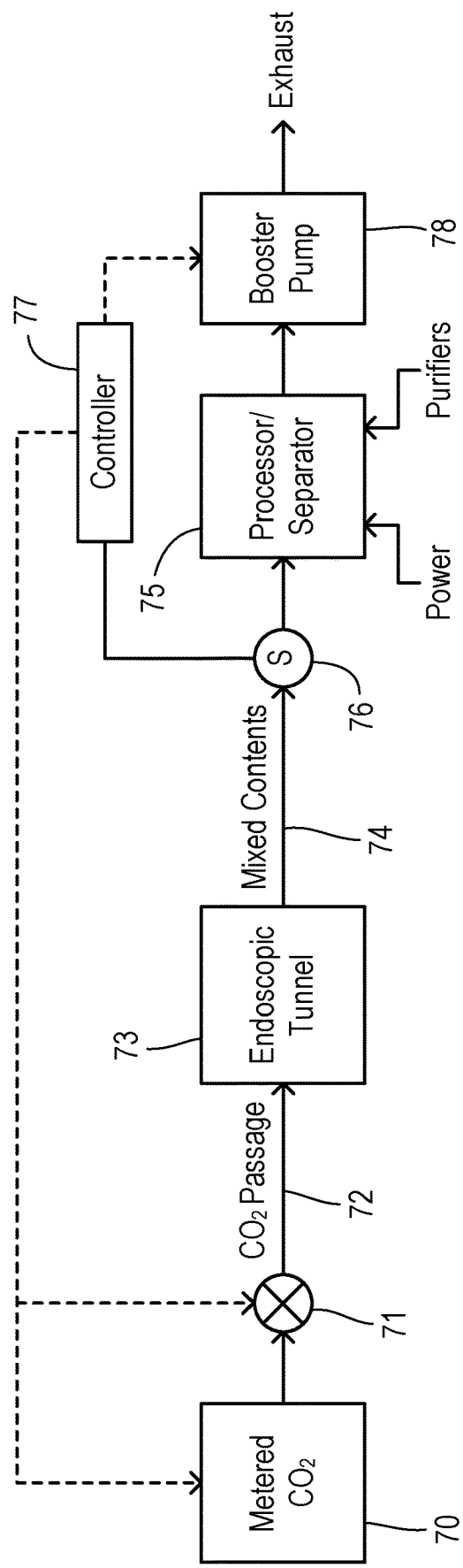
FIG. 9 is a block diagram showing an insufflation system according to one preferred embodiment of the present invention.

In some embodiments, active control of gas pressure and flow can be provided as shown in FIG. 9. A metered insufflation source 70 provides $CO_2$ gas to an supply valve/connector 71. A passage 72 (including the insufflation channel in the instrument and/or trocar) conveys the insufflation gas to dissected tunnel space 73. Removal channel 74 conveys mixed fluidic contents from space 73 to a processor/separator 75 for treatment. Depending upon the specific treatments, external power and/or purifiers may be provided to processor 75. A pressure sensor 76 senses a pressure of the fluidic contents within removal channel 74. Alternatively, the pressure could be sensed in processor 75. Active pressure regulation would not always be necessary if channel sizes and flow capacities are chosen appropriately. However, even with appropriate choices of channel sizes and flow capacities, active regulation may be useful or necessary in some embodiments.

A pressure signal from sensor 76 is provided to an electronic controller 77 for monitoring pressure and taking one or more actions to maintain the pressure within a desired range of pressure. For example, controller 77 can provide a command signal to source 70 in order to regulate the inlet pressure. Supply valve 71 could be electrically controllable so that controller 77 could modulate the supply or adjust a flow rate. In another embodiment, a booster pump 78 is coupled to an outlet of processor 75. If the pressure signal indicate insufficient flow through processor 75, then controller 77 may activate booster pump 78.

Figure 10:
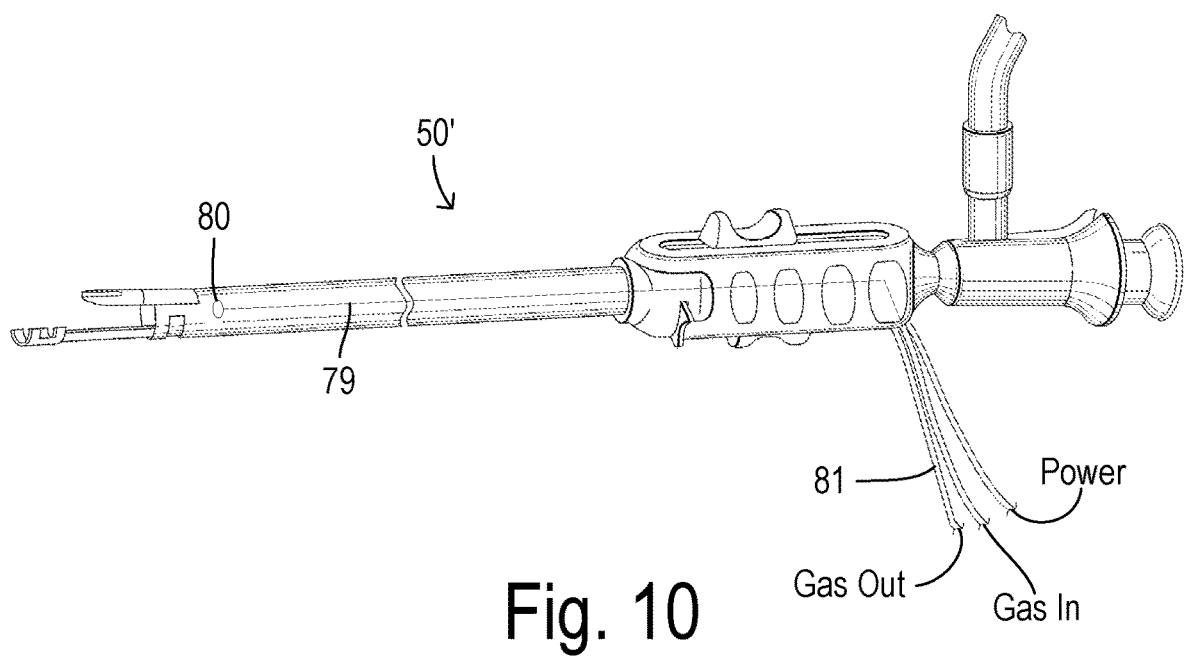
FIG. 10 schematically shows a modification of the cutting unit of FIG. 6.
Figure 11:
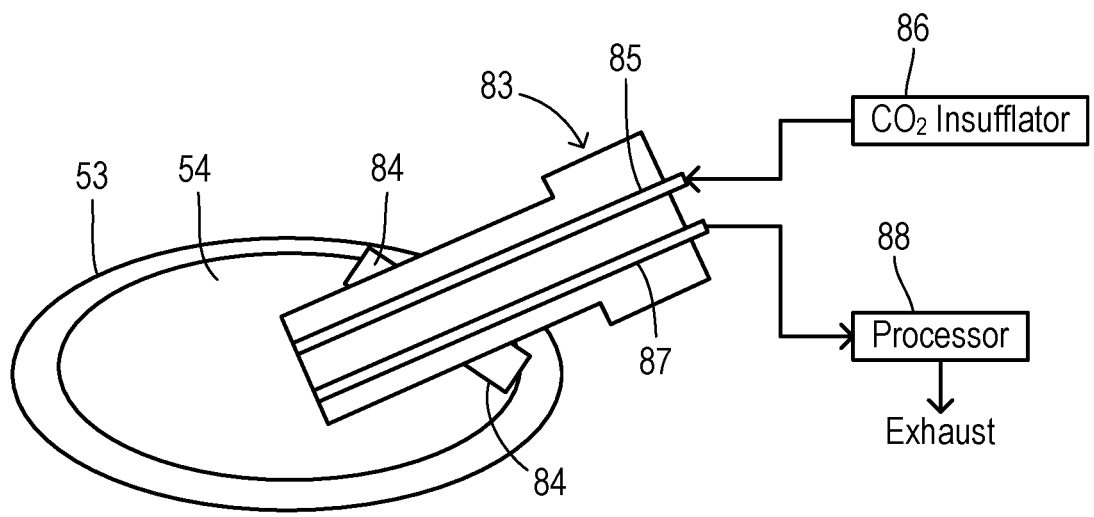
FIG. 11 schematically shows an insufflation system of the invention without a trocar.

FIG. 10 depicts a modification of the cutter unit 50 of FIG. 6. Cutter unit 50' is provided with a removal channel 79 between a distal inlet 80 and a proximal removal tube 81. Cutter unit 50' works according to a general arrangement shown in FIG. 11 wherein an endoscopic instrument 83 is inserted through an incision into dissected space 54. A sealing interface 84 between instrument 83 and body 53 may be comprised of a tight fit within the incision or a separate sealing component to ensure that fluidic contents do not leak from tunnel space 54. An insufflation channel 85 provides insufflation gas from a source 86 into space 54, and a removal channel 87 contained within instrument 83 conveys fluidic contents to a processor 88 to be treated prior to being exhausted.

Figure 12:
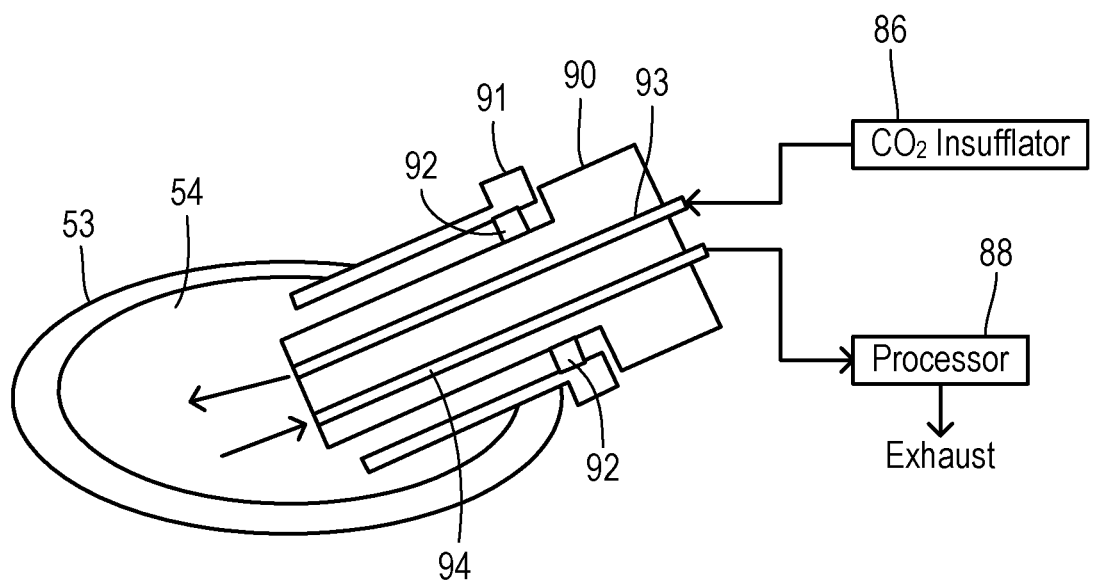
FIG. 12 schematically shows an insufflation system of the invention with a trocar wherein the delivery and collection of insufflation gas occur via the endoscopic instrument.

FIG. 12 shows another general arrangement wherein gas insertion and removal are both carried out within an endoscopic instrument and wherein a trocar is utilized. An endoscopic instrument 90 and a trocar 91 have a sealing interface 92. Likewise, trocar 91 has a sealing interface with the incision. An insufflation channel 93 provides insufflation gas from source 86 into space 54, and a removal channel 94 contained within instrument 83 conveys fluidic contents to a processor 88 to be treated prior to being exhausted.

Figure 13:
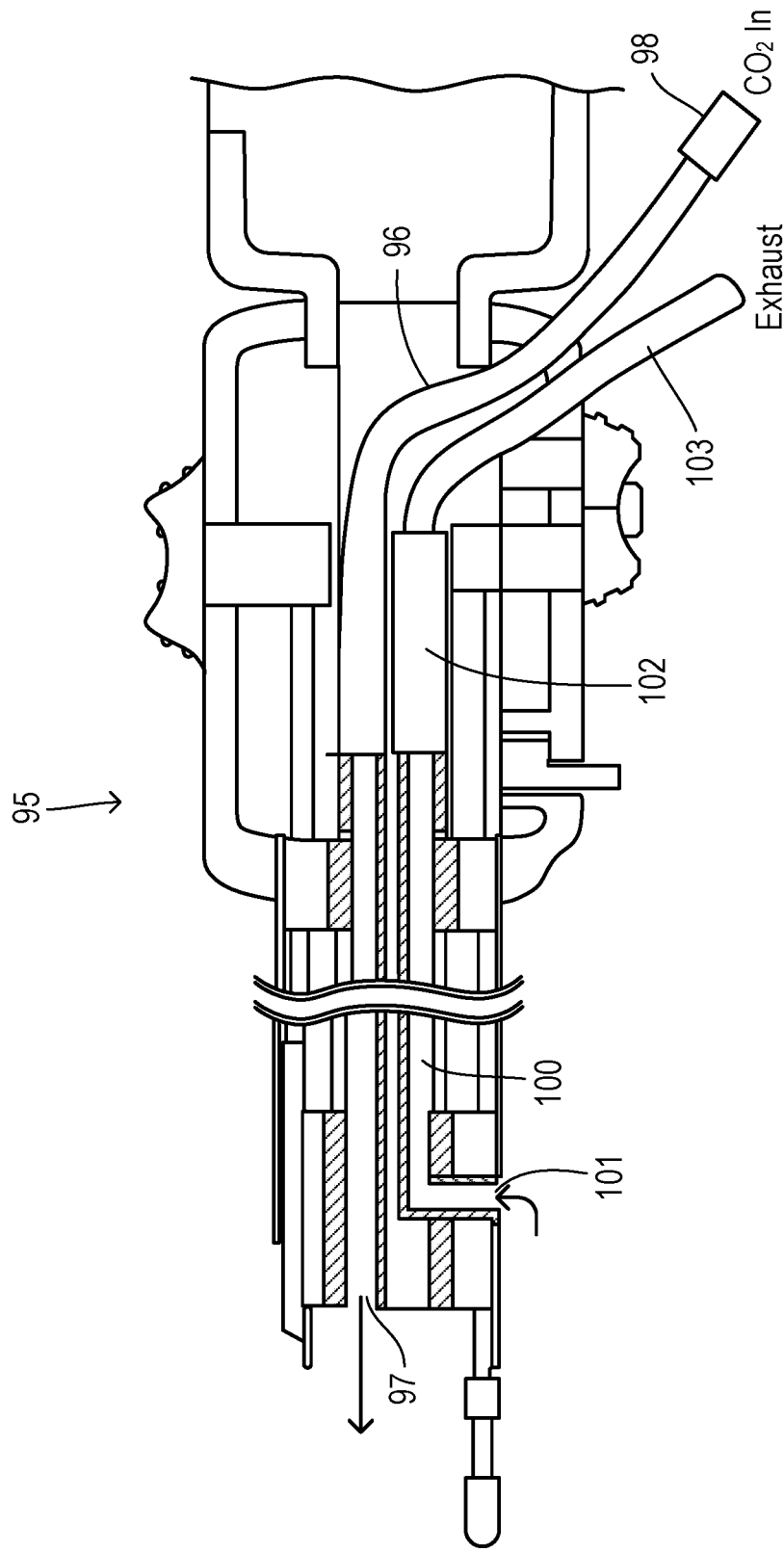
FIG. 13 is a side, partial cross-sectional view of a cutting unit with integrated insufflation and removal channels and an integrated separator/processor.
Figure 14:
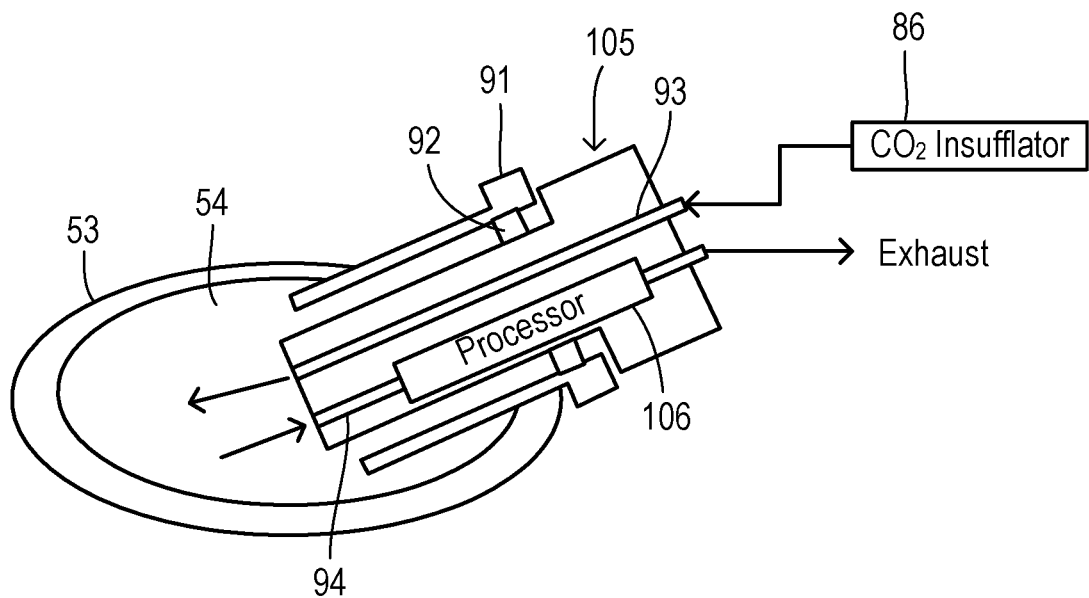
FIG. 14 schematically shows a sealed harvesting unit with integrated insufflation and removal channels and an integrated separator/processor.

FIG. 13 shows another embodiment of a cutter unit 95 containing an insufflation channel 96 between a distal outlet 97 and a line connector 98 for attaching to a gas supply line. A removal channel 100 evacuates fluidic contents from the dissected space at an inlet 101 and conveys them to a self-contained processor 102. Processor 102 can remove (e.g., filter or trap) and/or treat (e.g., disinfect) biological impurities as discussed above. An outlet tube 103 exhausts the processed outlet flow of processor 102 to ambient air. FIG. 14 shows a general arrangement for any endoscopic instrument similar to FIG. 12 except that an instrument 105 internally integrates a processor 106.

Figure 15:
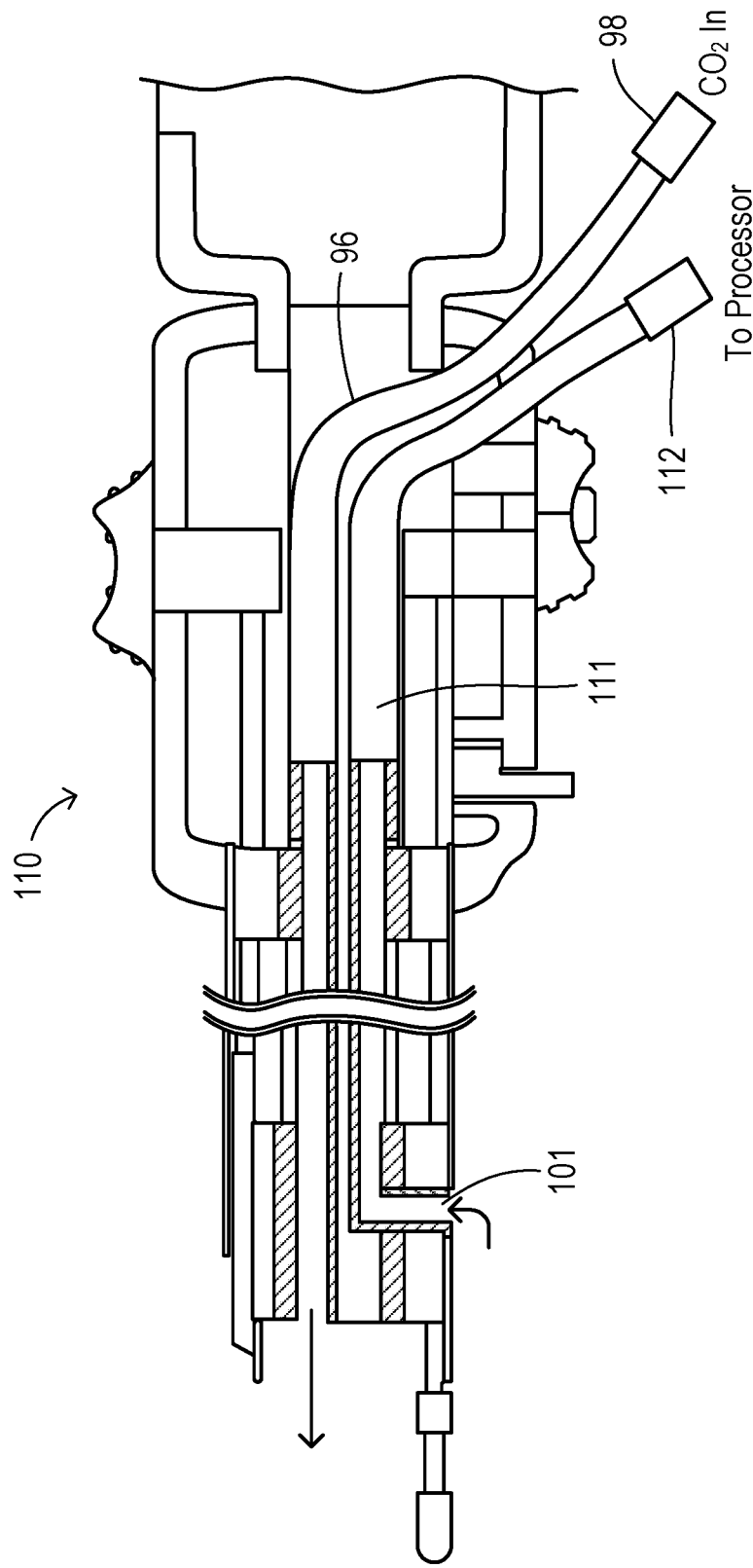
FIG. 15 is a side, partial cross-sectional view of a cutting unit with integrated insufflation and removal channels and without an integrated separator/processor.

FIG. 15 shows an embodiment of a cutter unit 110 that is similar to FIG. 13 except that an external processor is used. Thus, a removal channel 111 extends from distal inlet 101 to a line connector 98 adapted to connect to a processor/separator (not shown).

Figure 16:
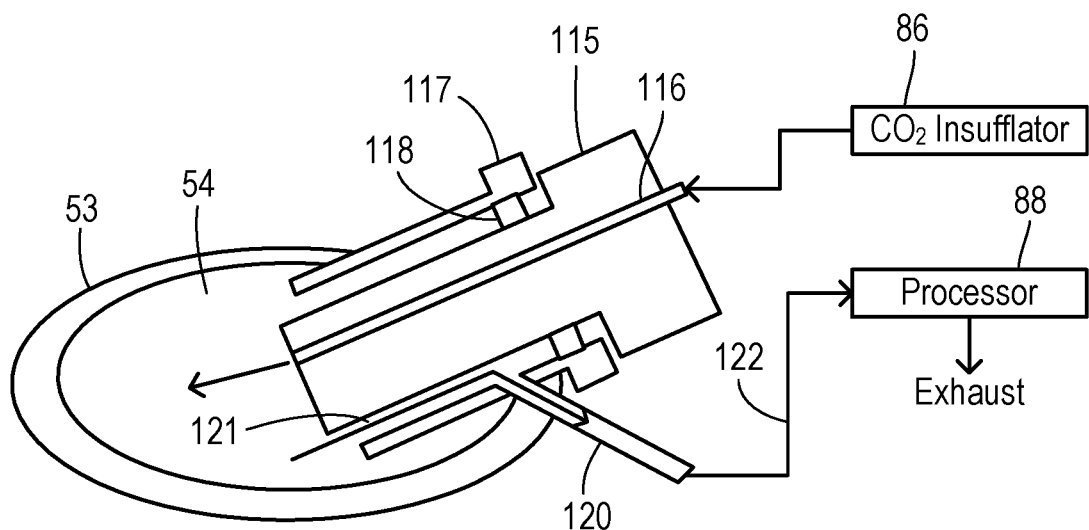
FIG. 16 schematically shows a sealed harvesting unit with integrated insufflation channel and a trocar with an integrated removal channel.
Figure 17:
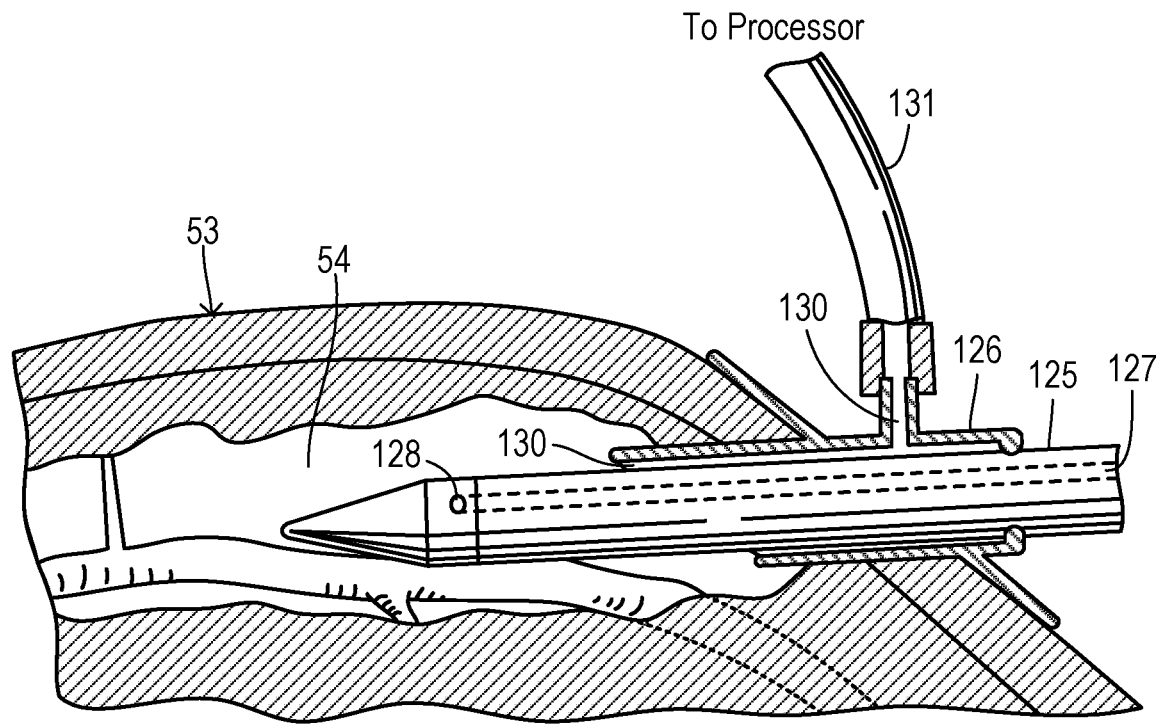
FIG. 17 is a side, partial cross-sectional view of a dissecting unit with a insufflation channel and a trocar with a removal channel.

In some embodiments, the insufflation and/or removal channels may be disposed in a trocar instead of the endoscopic instrument. FIG. 16 shows a general arrangement wherein endoscopic instrument 115 has an insufflation channel 116 for conveying gas from source 86 into tunnel 54. A trocar 117 has a sealing interface 118 with instrument 115. In order to evacuate fluidic contents from tunnel 54, trocar 117 has a removal channel 120 adapted to receive the fluidic contents via a gap between trocar 117 and instrument 115 and adapted to connect to a tube 122 to deliver the fluidic contents to processor 88. FIG. 17 shows an example of a dissector unit 125 inserted into a patient using a trocar 126. Dissector 125 has an insufflation channel 127 with a distal outlet 128 to inflate tunnel 54. Trocar 126 has an integrated removal channel 130 adapted to connect to a tube 131 to evacuate the fluidic contents to a processor (not shown).

Figure 18:
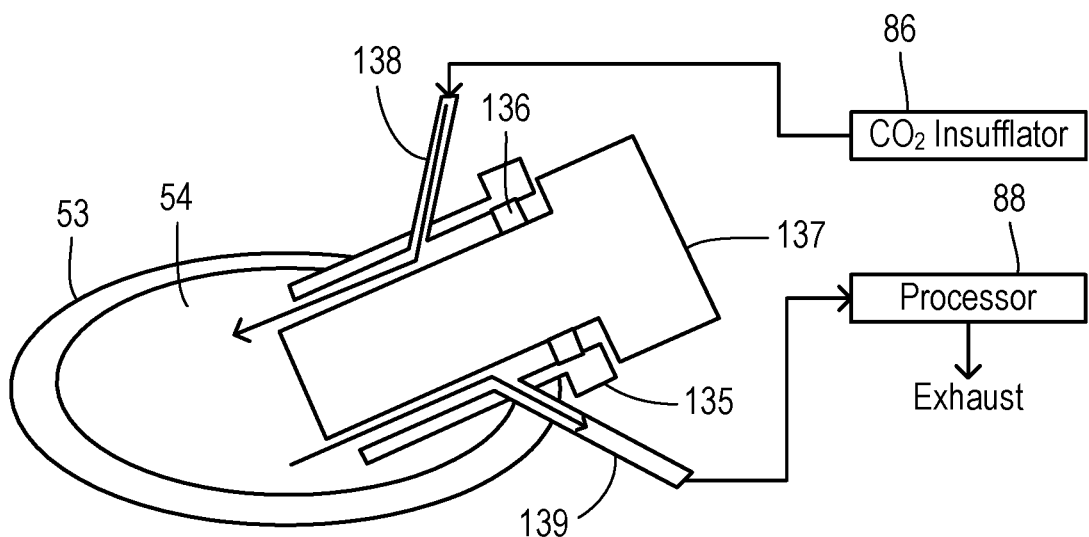
FIG. 18 schematically shows a sealed harvesting unit within a trocar, wherein the trocar has integrated insufflation and removal channels.

FIG. 18 shows a general arrangement wherein both supply and removal of insufflation gas are integrated into the trocar (e.g., insufflation is carried out separately from the endoscopic instrument). Thus, a trocar 135 is inserted through an incision providing access to tunnel 54. Trocar 135 has a sealing interface 136 with endoscopic instrument 137. Insufflation gas from source 86 is coupled to an insufflation channel 138 which is integrated in trocar 135 in order to inflate tunnel 54. Trocar 135 integrates a removal channel 139 for evacuating fluidic contents from tunnel 54 to processor 88.

Figure 19:
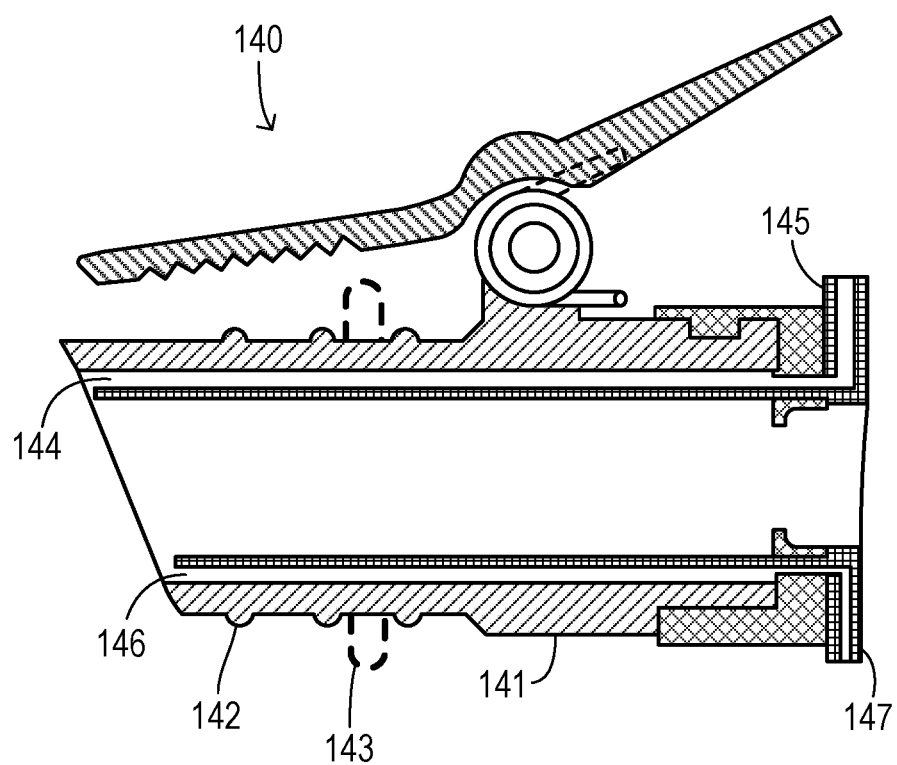
FIG. 19 is a cross-sectional view of a trocar showing integrated insufflation and removal channels in greater detail.

FIG. 19 shows a trocar 140 in greater detail. A main cylindrical body 141 of trocar 140 has ribs 142 or a flexible gasket 143 to provide a sealing interface with the patient's body at an incision. An insufflation channel 144 extends through body 141 from a distal end to a proximal tube connector 145. A removal channel 146 extends through body 141 from a distal end to a proximal tube connector 147.

What is claimed is:

1. A vessel harvesting apparatus for removing a blood vessel from a patient, comprising:
    an endoscopic instrument having a distal end with a vessel harvesting tip and having a proximal end with a handle;
    an insufflation channel configured to convey an insufflation gas subcutaneously into a dissected space within the patient;
    a removal channel configured to evacuate fluidic contents from the dissected space, wherein the fluidic contents include insufflation gas and biological impurities; and
    a processor coupled to the removal channel and configured to process the fluidic contents and retain at least some of the biological impurities and to exhaust the insufflation gas,
    wherein the removal channel is disposed within the endoscopic instrument.

2. The apparatus of claim 1 wherein the processor comprises a filter conducting the evacuated fluidic contents and configured to confine particles having a predetermined size.

3. The apparatus of claim 1 wherein the processor is comprised of a liquid trap conducting the evacuated fluidic contents and configured to divert liquids in the fluidic contents away from the exhausted insufflation gas.

4. The apparatus of claim 1 wherein the processor is comprised of a sterilizer.

5. The apparatus of claim 4 wherein the sterilizer is configured to treat the fluidic contents using at least one of heat, ultraviolet light, and a disinfectant substance.

6. The apparatus of claim 1 wherein the insufflation channel is disposed through the endoscopic instrument, extending from the proximal end to an outlet adjacent to the tip.

7. The apparatus of claim 1 wherein the removal channel is disposed through the endoscopic instrument, extending from an inlet adjacent to the tip to an outlet at the proximal end.

8. The apparatus of claim 1 further comprising a trocar configured to provide a sealed interface with an incision made to the patient, wherein the insufflation channel is integrated with the trocar.

9. The apparatus of claim 1 further comprising a pressure regulator configured to maintain a predetermined pressure of the insufflation gas.

10. A method of visualizing subcutaneous tissue while harvesting a blood vessel from a patient, comprising the steps of:
    inserting a tip of an endoscopic instrument subcutaneously into the patient, wherein the endoscopic instrument has an optical system providing a visual output for driving a video display;
    continuously delivering insufflation gas into a dissected space formed within the patient via an insufflation channel, wherein expelled insufflation gas inflates the dissected space;
    evacuating fluidic contents from the dissected space via a removal channel disposed within the endoscopic instrument to avoid overpressurization of the dissected space, wherein the fluidic contents include insufflation gas and biological impurities;
    processing the fluidic contents to retain at least some of the biological impurities; and
    exhausting the processed insufflation gas to ambient air without the retained biological impurities.

11. The method of claim 10 wherein the step of processing is comprised of filtering the evacuated fluidic contents to confine particles having a predetermined size in a filter media.

12. The method of claim 10 wherein the step of processing is comprised of trapping liquids in the evacuated fluidic contents and diverting the trapped liquids away from the exhausted insufflation gas.

13. The method of claim 10 wherein the step of processing is comprised of sterilizing the fluidic contents.

14. The method of claim 13 wherein the sterilizing is comprised of treating the fluidic contents using at least one of heat, ultraviolet light, and a disinfectant substance.

15. The method of claim 10 further comprising the step of regulating a pressure of the insufflation gas to maintain a predetermined pressure.

16. A device for performing endoscopic surgery on a patient, comprising:
an endoscopic instrument having a distal end with a surgical tip and having a proximal end with a handle, wherein the distal end is configured for insertion through a skin incision in the patient into a dissected space;
an insufflation channel configured to convey an insufflation gas subcutaneously into the dissected space;
a removal channel disposed within the endoscopic instrument, the removal channel configured to evacuate fluidic contents from the dissected space, wherein the fluidic contents include insufflation gas and biological impurities; and
a processor coupled to the removal channel to process the fluidic contents to retain at least some of the biological impurities and to exhaust the insufflation gas.

17. The device of claim 16 wherein the processor is comprised of a filter conducting the evacuated fluidic contents and configured to confine particles having a predetermined size.

18. The device of claim 16 wherein the processor is comprised of a
sterilizer for treating the fluidic contents using at least one of heat, ultraviolet light, and a disinfectant substance.

* * * * *